US005981214A

United States Patent [19]
Skoultchi

[11] Patent Number: 5,981,214
[45] Date of Patent: Nov. 9, 1999

[54] PRODUCTION OF PROTEINS USING HOMOLOGOUS RECOMBINATION

[75] Inventor: Arthur I. Skoultchi, Larchmont, N.Y.

[73] Assignee: Cell Genesys, Inc., Foster City, Calif.

[21] Appl. No.: 08/467,244

[22] Filed: Jun. 6, 1995

Related U.S. Application Data

[62] Continuation of application No. 08/102,390, Aug. 5, 1993, which is a continuation of application No. 07/787,390, filed as application No. PCT/US90/06346, Nov. 6, 1990, abandoned, which is a continuation-in-part of application No. 07/432,069, Nov. 6, 1989, abandoned.

[51] Int. Cl.$^6$ .................................................. C12N 15/00
[52] U.S. Cl. ....................... 435/69.1; 435/70.1; 435/355; 435/357; 435/358; 435/364; 435/365.1; 435/455; 435/463; 435/464; 536/24.1
[58] Field of Search ................................ 435/69.1, 172.3, 435/352, 357, 358, 364, 365.1, 366, 371, 354, 455, 463, 464, 70.1, 355; 536/24.1, 23.1

[56] References Cited

U.S. PATENT DOCUMENTS

| | | | |
|---|---|---|---|
| 4,634,665 | 1/1987 | Axel et al. ............................. | 435/69.1 |
| 4,656,134 | 4/1987 | Ringold .................................... | 435/91 |
| 4,950,599 | 8/1990 | Bertling ................................. | 435/456 |
| 5,272,071 | 12/1993 | Chappel .................................... | 435/6 |

FOREIGN PATENT DOCUMENTS

| | | |
|---|---|---|
| 0 278 659 | 8/1988 | European Pat. Off. . |
| 0 320 500 | 6/1989 | European Pat. Off. . |
| WO 88/05077 | 7/1988 | WIPO . |
| WO 89/09256 | 10/1989 | WIPO . |
| WO 90/06363 | 6/1990 | WIPO . |
| WO 90/11354 | 10/1990 | WIPO . |
| WO 90/14092 | 11/1990 | WIPO . |
| WO 91/02070 | 2/1991 | WIPO . |
| WO 91/06666 | 5/1991 | WIPO . |
| 9109955 | 7/1991 | WIPO . |
| WO 91/09955 | 7/1991 | WIPO . |
| WO 93/09222 | 5/1993 | WIPO . |

OTHER PUBLICATIONS

Rubnitz et al Mol. Cell. Biol 4:2253,1984.
Kamarck et al PNAS 84: 5350,1987.
Muller et al Eur. J. Biochem 176:485,1988.
Thomas et al Cell 51: 503,1987.
Palmer et al PNAS 84: 1055,1987.
Boshers et al Sequence Species Transcript & Transl. pp. 511–520,1985.
Foecking et al Gene 45: 101,1986.
Nandi et al PNAS 85: 3845,1988.
Frohman et al Cell 56: 145,1989.
Smithies et al Nature 317: 231,1985.
Nelson et al J of Mol. Appl Gen 2(6): 563,1984.
Thompson et al Cell 56: 313,1989.
Anderson Science 226: 401,1984.
Anderson (1984), "Prospects for Human Gene Therapy," Science 226:401–409.

Foecking and Hofstetter, (1986), "Powerful and versatile enhancer–promoter unit for mammalian expression vectors," Gene 45:101–105.
Frohman et al. (1989), "Cut, Paste, and Save: New Approaches to Altering Specific Genes in Mice," Cell 56:145–147.
Janniere et al. (1985), "Stable gene amplification in the chromosome of *Bacillus subtilis*", Gene 40:47–55.
Johnson et al. (1989), "Targeting of Nonexpressed Genes in Embryonic Stem Cells Via Homologous Recombination", Science 245:1234–1236.
Kamarck et al. (1987), "Carcinoembryonic antigen family: Expression in a mouse L–cell transfectant and characterization of a partial cDNA in bacteriophage λgt11," PNAS 84:5350–5354.
Kim and Smithies (1988), "Recombinant fragment assay for gene targeting based on the polymerase chain reaction," Nucleic Acids Res. 16:8887–8903.
Larsen et al. (1986), "Repression mediates cell–type–specific expression of the rat growth hormone gene", Proc. Natl. Acad. Sci. U.S.A. 83:8283–8287.
Le Mouellic et al. (1990), "Targeted replacement of the homeobox gene Hox–3.1 by the *Escherichia coli lacZ* in mouse chimeric embryos", Proc. Natl. Acad. Sci. U.S.A. 87:4712–4716.
Lewin, B. in: Genes, 1983, Oxford University Press, NY, NY, pp. 188–194.
Liskay et al. (1984), "Homologous Recombination between Repeated Chromosomal Sequences in Mouse Cells," Cold Spring Harbor Symp. Quant. Biol. 49:183–189.
Mansour et al. (1988), "Disruption of the proto–oncogene int–2 in mouse embryo–derived stem cells: a general strategy for targeting mutations to non–selectable genes," Nature 336:348–352.
Muller et al. (1988), "Enhancer sequences and the regulation of gene transcription," Eur. J. Biochem. 176:485–495.
Murnane and Yezzi (1988), "Association of High Rate of Recombination with Amplification of Dominant Selectable Gene in Human Cells," Somatic Cell and Molecular Genetics 14:273–286.
Nandi et al. (1988), "Regulated expression of genes inserted at the human chromosomal β–globin locus by homologous recombination," Proc. Natl. Acad. Sci. U.S.A. 85:3845–3849.

(List continued on next page.)

*Primary Examiner*—James Ketter
*Assistant Examiner*—Irem Yucel
*Attorney, Agent, or Firm*—Pennie & Edmonds LLP

[57] ABSTRACT

Methods and compositions are provided for expression of mammalian genes in culture. An amplifiable gene is introduced by homologous recombination in juxtaposition to a target gene, the resulting combination of amplifiable gene and target gene transferred to a convenient host and the target gene amplified by means of the amplifiable gene. The resulting expression host may then be grown in culture with enhanced expression of the target gene.

20 Claims, 6 Drawing Sheets

OTHER PUBLICATIONS

Nelson et al. (1984), "Metaphase Chromosome Transfer of Introduced Selectable Markers," J. of Mol. Appl. Gen. 2:563–577.

Old and Primrose, In: *Studies in Microbiology*, vol. 2. "Principles of Gene Manipulation: An Introduction to Genetic Engineering," 2nd Ed., 1981, University of California Press, p. 194.

Palmer et al. (1987), "Efficient retrovirus–mediated transfer and expression of a human adenosine deaminase gene in diploid skin fibroblasts from an adenosine deaminase–deficient human," Proc. Natl. Acad. Sci. U.S.A. 84:1055–1059.

Palmer et al. (1991), "Genetically modified skin fibroblasts persist long after transplantation but gradually inactivate introduced genes," Proc. Natl. Acad. Sci. U.S.A. 88:1330–1334.

Raibaud et al. (1984), "A technique for integrating any DNA fragment into the chromosome of *Escherichia coli*", Gene 29:231–241.

Rubnitz and Subramani (1984), "The Minimum Amount of Homology Required for Homologous Recombination in Mammalian Cells," Mol. Cell. Biol. 4:2253–2258.

Sambrook et al. (1989), "Molecular Cloning: A Laboratory Manual" (Cold Spring Harbor Press, 1989) pp. 16.3–16.5.

Smithies et al. (1985), "Insertion of DNA sequences into the human chromosomal β–globin locus by homologous recombination", Nature 317:230–234.

Song, et al. (1987), "Accurate modification of a chromosomal plasmid by homologous recombination in human cells," Proc. Natl. Acad. Sci. U.S.A. 84:6820–6824.

Thomas and Capecchi (1987), "Site–Directed Mutagenesis by Gene Targeting in Mouse Embryo–Derived Stem Cells," Cell 51:503–512.

Thompson et al., (1989), "Germ Line Transmission and Expression of a Corrected HPRT Gene Produced by Gene Targeting in Embryonic Stem Cells", Cell 56:313–321.

Urlaub and Chasin (1980), "Isolation of Chinese hamster cell mutants deficient in dihydrofolate reductase activity," Proc. Natl. Acad. Sci. U.S.A. 77:4216–4220.

Watson et al., in: Recombinant DNA, A Short Course, 1983, W.H. Freedman & Co., NY, NY, pp. 41, 47.

Weidle et al. (1988), "Amplified expression constructs for human tissue–type plasminogen activator in Chinese hamster ovary cells: instability in the absence of selective pressure," Gene 66:193–203.

Zhu et al. (1986), "Construction of stable laboratory and industrial yeast strains expressing a foreign gene by integrative transformation using a dominant selection system" Gene 50:225–237.

American Type Culture Collection Catalog of Cell Lines and Hybridomas, Sixth Edition, 1988, p. 151.

Athwal et al. (1977), "Serial transfer of a human gene to rodent cells by sequential chromosome–mediated gene transfer," Proc. Natl. Acad. Sci. USA 74:2943–2947.

Baker and Shulman (1988), "Homologous Recombination between Transferred and Chromosomal Immunoglobulin κ Genes," Mol. Cell. Biol. 8:4041–4047.

Capecchi (1989), "The New Mouse Genetics: Altering the Genome by Gene Targeting," Trends in Genetics 5:70–76.

Connors et al. (1988), "DHFR Coamplification of t–PA in DHFR+ Bovine Endothelial Cells: In Vitro Characterization of the Purified Serine Protease," DNA 7:651–661.

Fuerst et al. (1986), "Eukaryotic transient–expression system based on recombinant vaccinia virus that synthesizes bacteriophage t7 RNA polymerase," Proc. Natl. Acad. Sci. U.S.A. 83:8122–8126.

Goldfarb et al. (1982), "Isolation and preliminary characterization of a human transforming gene from T24 bladder carcinoma cells," Nature 296:404–409.

Kaufman et al. (1985), "Coamplification and Coexpression of Human Tissue–Type Plasminogen Activator and Murine Dihydrofolate Reductase Sequences in Chinese Hamster Ovary Cells, " Mol. Cell. Biol. 5:1750–1759.

Kaufman et al. (1986), "Selection and amplification of heterologous genes encoding adenosine deaminase in mammalian cells," Proc. Natl. Acad. Sci. U.S.A. 83:3136–3140.

Kaufman, "High Level Production of Proteins in Mammalian Cells," In: Genetic Engineering: Principles and Methods (vol. 9) (Plenum Press 1987).

Klobutcher and Ruddle (1981), "Chromosome Mediated Gene Transfer," Ann. Rev. Biochem. 50:533–534.

Lewis and Srinivasan (1983), "Chromosome–Mediated Gene Transfer of Hydroxyurea Resistance and Amplification of Ribonucleotide Reductase Activity," Mol. Cell Biol. 3:1053–1061.

Lowy et al. (1980) "Isolation of Transforming DNA: Cloning the Hamster aprt Gene," Cell 22:817–823.

Michel et al. (1985), "Expression of Amplified Hepatitis B Virus Surface Antigen Genes in Chinese Hamster Ovary Cells," Biotechnology 3:561–566.

Saxon and Stanbridge (1987), "Transfer and Selective Retention of Single Specific Human Chromosomes via Microcell–Mediated Chromosome Transfer," Meth. Enz. 151:313–325.

Scahill et al. (1983), "Expression and characterization of the product of a human immune interferon cDNA gene in Chinese hamster ovary cells," Proc. Natl. Acad. Sci. U.S.A. 80:4654–4658.

Mansour, et al. (1988) *Nature* 336:348–352 "Disruption of the proto–oncogene int–2 in mouse embryo–derived stem cells: a general strategy for targeting mutations to non–selectable genes".

Weidle, et al. (1988) *Gene* 66:193–203 "Amplified expression constructs for human tissue–type plasminogen activator in Chinese hamster ovary cells: instability in the absence of selective pressure".

Murnane and Yezzi (1988) *Somatic Cell and Molecular Genetics* 14:273–286 "Association of High Rate of Recombination with Amplification of Dominant Selectable Gene in Human Cells".

Thomas and Capecchi (1987) *Cell* 51:503–512 "Site–Directed Mutagenesis by Gene Targeting in Mouse Embryo–Derived Stem Cells".

Song, et al. (1987) *P.N.A.S. USA* 84:6820–6824 "Accurate modification of a chromosomal plasmid by homologous recombination in human cells".

Liskay, et al. (1984) *C.S.H.S.Q.B.* 49:183–189 "Homologous Recombination between Repeated Chromosomal Sequences in Mouse Cells".

Rubnitz and Subramani (1984) *Mol. and Cell. Biol.* 4:2253–2258 "The Minimum Amount of Homology Required for Homologous Recombination in Mammalian Cells".

Kim and Smithies (1988) *N.A.R.* 16:8887–8903 "Recombinant fragment assay for gene targeting based on the polymerase chain reaction".

Urlaub, et al. (1980) *P.N.A.S. USA* 77(7):4216–4220 "Isolation of Chinese hamster cell mutants deficient in dihydrofolate reductase activity".

Kamarck, et al. (1987) *P.N.A.S. USA* 84:5350–5354 "Carcinoembryonic antigen family: expression in a mouse L–cell transfectant and characterization of a partial cDNA in bacteriophage λgt11".

Liskay et al CSH SQB 49:183,1984.
Anderson Science 226:401,1984.
Thomas et al Cell 51: 503,1987.
Song et al PNAS 84: 6820,1987.
Mansour et al Nature 336: 348,1988.
Palmer et al PNAS 88: 1330,1991.

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
       (A) LENGTH: 144 base pairs
       (B) TYPE: nucleic acid
       (C) STRANDEDNESS: single
       (D) TOPOLOGY: unknown (ii) MOLECULE TYPE: DNA (genomic)

(xi) SEQUENCE DESCRIPTION: SEQ ID NO:1:

```
TGCGGCCGCG GTTATCGATG ACGCGTCCTC GAGCAAGCTT CTCTAGACGG TCACCTTCCG      60

CGGCCGCTGT ACTCGAACGC CGGCGCCAAT AGCTACTGCG CAGGAGCTCG TTCGAAGAGA     120

TCTGCCAGTG GAAGGCGCCG GCGA                                           144
```

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: unknown (ii) MOLECULE TYPE: DNA (genomic)

(xi) SEQUENCE DESCRIPTION: SEQ ID NO:2:

```
GCGGCCTCGG CCTCTGCATA                                                 20
```

(2) INFORMATION FOR SEQ ID NO:3:

(i) SEQUENCE CHARACTERISTICS:
       (A) LENGTH: 20 base pairs
       (B) TYPE: nucleic acid
       (C) STRANDEDNESS: single
       (D) TOPOLOGY: unknown (ii) MOLECULE TYPE: DNA (genomic)

(xi) SEQUENCE DESCRIPTION: SEQ ID NO:3:

```
CATCTCCCCT CTGGAGTGGA                                                 20
```

(2) INFORMATION FOR SEQ ID NO:4:

(i) SEQUENCE CHARACTERISTICS:
       (A) LENGTH: 36 base pairs
       (B) TYPE: nucleic acid
       (C) STRANDEDNESS: single
       (D) TOPOLOGY: unknown (ii) MOLECULE TYPE: DNA (genomic)

(xi) SEQUENCE DESCRIPTION: SEQ ID NO:4:

```
CTGGGTTGCT GAGTTCCGCA AAGTAGCTGG GTCTGG                               36
```

(2) INFORMATION FOR SEQ ID NO:5:

(i) SEQUENCE CHARACTERISTICS:
       (A) LENGTH: 36 base pairs
       (B) TYPE: nucleic acid
       (C) STRANDEDNESS: single
       (D) TOPOLOGY: unknown (ii) MOLECULE TYPE: DNA (genomic)

(xi) SEQUENCE DESCRIPTION: SEQ ID NO:5:

CGGGGGTCGG GGCTGTTATC TGCATGTGTG CGTGCG                              36

(2) INFORMATION FOR SEQ ID NO:6:

(i) SEQUENCE CHARACTERISTICS:
            (A) LENGTH: 26 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO:6:

CGCCAAGCTT GGCCATTGCA TACGTT                                         26

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO:7:

GAGGTCTAGA CGGTTCACTA AACGAGCTCT                                     30

(2) INFORMATION FOR SEQ ID NO:8:

(i) SEQUENCE CHARACTERISTICS:
            (A) LENGTH: 29 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO:8:

GGACGCGTGG ATCCAGACAT GATAAGATA                                      29

(2) INFORMATION FOR SEQ ID NO:9:

(i) SEQUENCE CHARACTERISTICS:
            (A) LENGTH: 29 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO:9:

GGACGCGTCA GCTGTGGAAT GTGTGTCAG                                      29

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: unknown (ii) MOLECULE TYPE: DNA (genomic)

(xi) SEQUENCE DESCRIPTION: SEQ ID NO:10:

AAGCAGAGCT CGTTTAGTGA ACCG                                           24

-continued (2) INFORMATION FOR SEQ ID NO:11:

(i) SEQUENCE CHARACTERISTICS:
       (A) LENGTH: 24 base pairs
       (B) TYPE: nucleic acid
       (C) STRANDEDNESS: single
       (D) TOPOLOGY: unknown (ii) MOLECULE TYPE: DNA (genomic)

(xi) SEQUENCE DESCRIPTION: SEQ ID NO:11:

TGAGCGTGAG TTCTGTGGAA TGTG                                                24

PRODUCTION OF PROTEINS USING HOMOLOGOUS RECOMBINATION

This application is a continuation of application Ser. No. 08/102,390, filed Aug. 5, 1993, pending, which is a continuation of application Ser. No. 07/787,390, filed Nov. 4, 1991 as the national stage of International application PCT/US90/06346 filed Nov. 6, 1990, now abandoned, which is a continuation-in-part of application Ser. No. 432,069, filed Nov. 6, 1989, now abandoned.

INTRODUCTION

1. Technical Field

The field of this invention is the expression of mammalian proteins.

2. Background

The discoveries of restriction enzymes, cloning, sequencing, reverse transcriptase, and monoclonal antibodies has resulted in extraordinary capabilities in isolating, identifying, and manipulating nucleic acid sequences. As a result of these capabilities, numerous genes and their transcriptional control elements have been identified and manipulated. The genes have been used for producing large amounts of a desired protein in heterologous hosts (bacterial and eukaryotic host cell systems).

In many cases, the process of obtaining coding sequences and eliciting their expression has been a long and arduous one. The identification of the coding sequence, either cDNA or genomic DNA, has frequently involved the construction of libraries, identification of fragments of the open reading frame, examining the flanking sequences, and the like. In mammalian genes where introns are frequently encountered, in many instances, the coding region has been only small fraction of the total nucleic acid associated with the gene. In other cases, pseudogenes or multi-membered gene families have obscured the ability to isolate a particular gene of interest. Nevertheless, as techniques have improved, there has been a continuous parade of successful identifications and isolation of genes of interest.

In many situations one is primarily interested in a source of the protein product. The cell type in the body which produces the protein is frequently an inadequate source, since the protein may be produced in low amounts, the protein may only be produced in a differentiated host cell which is only difficultly grown in culture, or the host cell, particularly a human cell, is not economic or efficient in a culture process for production of the product. There is, therefore, significant interest in developing alternative techniques for producing proteins of interest in culture with cells which provide for economic and efficient production of the desired protein and, when possible, appropriate processing of the protein product.

Relevant Literature

Mansour et al., *Nature,* 336:348–352 (1988), describe a general strategy for targeting mutations to non-selectable genes. Weidle et al., *Gene,* 66:193–203, (1988), describe amplification of tissue-type plasminogen activator with a DHFR gene and loss of amplification in the absence of selective pressure. Murnane and Yezzi, *Somatic Cell and Molecular Genetics,* 14:273–286, (1988), describe transformation of a human cell line with an integrated selectable gene marker lacking a transcriptional promoter, with tandem duplication and amplification of the gene marker. Thomas and Capecchi, *Cell,* 51:503–512, (19871, describe site-directed mutagenesis by gene targeting in mouse embryo-derived stem cells. Song et al., *Proc. Natl. Acad. Sci. USA,* 84:6820–6824, (1987), describe homologous recombination in human cells by a two staged integration. Liskay et al., "Homologous Recombination Between Repeated Chromosomal Sequences in Mouse Cells," Cold Spring Harbor, *Symp. Quant. Biol.* 49:13–189, (1984), describe integration of two different mutations of the same gene and homologous recombination between the mutant genes. Rubnitz and Subramani, *Mol. and Cell. Biol.* 4:2253–2258, (1984), describe the minimum amount of homology required for homologous recombination in mammalian cells. Kim and Smithies, *Nucl. Acids. Res.* 16:8887–8903, (1988), describe an assay for homologous recombination using the polymerase chain reaction.

SUMMARY OF THE INVENTION

Expression of mammalian proteins of interest is achieved by employing homologous recombination for integration of an amplifiable gene and other regulatory sequences in proximity to a gene of interest without interruption of the production of a proper transcript. The region comprising the amplifiable gene and the gene of interest may be amplified, the genome fragmented and directly or indirectly transferred to an expression host for expression of the target protein. If not previously amplified, the target region is then amplified, and the cell population screened for cells producing the target protein. Cells which produce the target protein at high and stable levels are expanded and used for expression of the target protein.

DESCRIPTION OF SPECIFIC EMBODIMENTS

Figure 1:
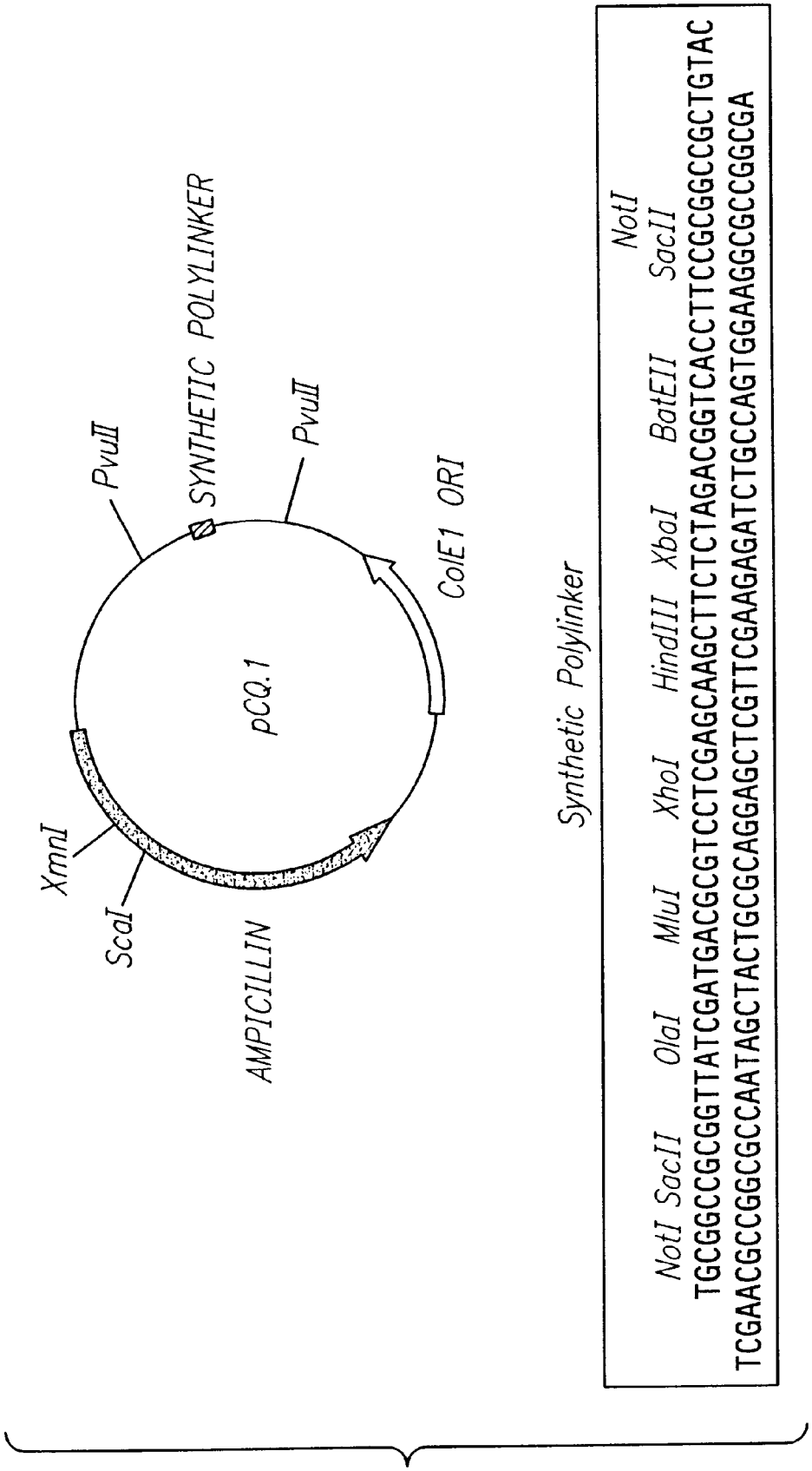
FIG. 1 is a diagrammatic illustration of the plasmid pCG.1 showing the sequence (SEQ ID NO:1) of the modified polylinker.

Methods and compositions are provided for production of mammalian proteins of interest in culture. The method employs homologous recombination in a host cell for integrating an amplifiable gene in the vicinity of a target gene, which target gene encodes the protein of interest. The region comprising both the amplifiable gene and target gene will be referred to as the amplifiable region. The resulting transformed primary cells may now be subjected to conditions which select for amplification, or the amplification may be performed subsequently. "Transform" includes transform, transfect, transduce, conjugation, fusion, electroporation or any other technique for introducing DNA into a viable cell. The chromosomes or DNA of the transformed cells are then used to transfer the amplifiable region into the genome of secondary expression host cells, where the target region, if not previously amplified sufficiently or at all, is further amplified. The resulting cell lines are screened for production of the target protein and secondary cell lines selected for desired levels of production, which cells may be expanded and used for production of the desired protein in culture.

The primary cell may be any mammalian cell of interest, particularly mammalian cells which do not grow readily in culture, more particularly primate cells, especially human cells, where the human cells may be normal cells, including embryonic or neoplastic cells, particularly normal cells. various cell types may be employed as the primary cells, including fibroblasts, particularly diploid skin fibroblasts, lymphocytes, epithelial cells, neurons, endothelial cells, or other somatic cells, or germ cells. Of particular interest are skin fibroblasts, which can be readily propagated to provide for large numbers of normal cells, embryonic kidney cells, and the like. These cells may or may not be expressing the gene of interest. In those instances where the target gene is inducible or only expressed in certain differentiated cells, one may select cells in which the target gene is expressed, which may require immortalized cells capable of growth in culture.

A number of amplifiable genes exist, where by appropriate use of a selection agent, a gene integrated in the genome will be amplified with adjacent flanking DNA. Amplifiable genes include dihydrofolate reductase, metallothionein-I and -II, preferably primate metallothionein genes, adenosine deaminase, ornithine decarboxylase, etc. The amplifiable gene will have transcriptional signals which are functional in the secondary or expression host and desirably be functional in the primary host, particularly where amplification is employed in the primary host or the amplifiable gene is used as a marker.

The target genes may be any gene of interest, there already having been a large number of proteins of interest identified and isolated with continual additions to the list. Proteins of interest include cytokines, such as interleukins 1–10; growth factors such as EGF, FGF, PDGF, and TGF; somatotropins; growth hormones; colony stimulating factors, such as G-, M-, and GM-CSF; erythropoietin; plasminogen activators, such as tissue and urine; enzymes, such as superoxide dismutase; interferons; T-cell receptors; surface membrane proteins; insulin; lipoproteins; $\alpha_1$-antitrypsin; CD proteins, such as CD3, 4, 8, 19; clotting factors, e.g., Factor VIIIc and von Willebrands factor; anti-clotting factors, such as Protein C; atrial naturetic factor; tumor necrosis factor; transport proteins; homing receptors; addressins; regulatory proteins; etc.

For homologous recombination, constructs will be prepared where the amplifiable gene will be flanked on one or both sides with DNA homologous with the DNA of the target region. The homologous DNA will generally be within 100 kb, usually 50 kb, preferably about 25 kb, of the transcribed region of the target gene, more preferably within 2 kb of the target gene. By gene is intended the coding region and those sequences required for transcription of a mature mRNA. The homologous DNA may include the 5'-upstream region comprising any enhancer sequences, transcriptional initiation sequences, the region 5' of these sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcription termination region, or the region 3' of this region. The homologous regions may extend over all or a portion of the target gene or be outside the target gene comprising all or a portion of the transcriptional regulatory regions and/or the structural gene. For the most part, the homologous sequence will be joined to the amplifiable gene, proximally or distally. Usually a sequence other than the wild-type sequence normally associated with the target gene will be used to separate the homologous sequence from the amplifiable gene on at least one side of the amplifiable gene. Some portion of the sequence may be the 5' or 3' sequence associated with the amplifiable gene, as a result of the manipulations associated with the amplifiable gene.

The homologous regions flanking the amplifiable gene need not be identical to the target region, where in vitro mutagenesis is desired. For example, one may wish to change the transcriptional initiation region for the target gene, so that a portion of the homologous region might comprise nucleotides different from the wild-type 5' region of the target gene. Alternatively, one could provide for insertion of a transcriptional initiation region different from the wild-type initiation region between the wild-type initiation region and the structural gene. Similarly, one might wish to introduce various mutations into the structural gene, so that the homologous region would comprise mismatches, resulting in a change in the encoded protein. For example, a signal leader sequence would be introduced in proper reading frame with the target gene to provide for secretion of the target protein expression product. Alternatively, one might change the 3' region, e.g., untranslated region, polyadenylation site, etc. of the target gene. Therefore, by homologous recombination, one can provide for maintaining the integrity of the target gene, so as to express the wild-type protein under the transcriptional regulation of the wild-type promoter or one may provide for a change in transcriptional regulation, processing or sequence of the target gene. In some instances, one may wish to introduce an enhancer in relation to the transcriptional initiation region, which can be provided by, for example, integration of the amplifiable gene associated with the enhancer in a region upstream from the transcriptional initiation regulatory region or in an intron or even downstream from the target gene.

In order to prepare the subject constructs, it will be necessary to know the sequence which is targeted for homologous recombination. While it is reported that a sequence of 14 bases complementary to a sequence in a genome may provide for homologous recombination, normally the individual flanking sequences will be at least about 150 bp, and may be 12 kb or more, usually not more than about 8 kb. The size of the flanking regions will be determined by the size of the known sequence, the number of sequences in the genome which may have homology to the site for integration, whether mutagenesis is involved and the extent of separation of the regions for mutagenesis, the particular site for integration, or the like.

The integrating constructs may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like. Usually the construct will be carried on a cloning vector comprising a replication system functional in a prokaryotic host, e.g., *E. coli*, and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc.

Once the construct is prepared, it may then be used for homologous recombination in the primary cell target. Various techniques may be employed for integrating the construct into the genome of the primary cell without being joined to a replication system functional in the primary host. See for example, U.S. Pat. No. 4,319,216, as well as the references cited in the Relevant Literature section. Alternatively, the construct may be inserted into an appropriate vector, usually having a viral replication system, such as SV40, bovine papilloma virus, adenovirus, or the like. The linear DNA sequence vector may also have a selectable marker for identifying transfected cells. Selectable markers include the neo gene, allowing for selection with G418, the herpes tk gene for selection with HAT medium, gpt gene with mycophenolic acid, complementation of an auxotrophic host, etc.

The vector may or may not be capable of stable maintenance in the host. Where the vector is capable of stable maintenance, the cells will be screened for homologous integration of the vector into the genome of the host, where various techniques for curing the cells may be employed. Where the vector is not capable of stable maintenance, for example, where a temperature sensitive replication system is employed, one may change the temperature from the permissive temperature to the non-permissive temperature, so that the cells may be cured of the vector. In this case, only those cells having integration of the construct comprising the amplifiable gene and, when present, the selectable marker, will be able to survive selection.

Where a selectable marker is present, one may select for the presence of the construct by means of the selectable marker. Where the selectable marker is not present, one may select for the presence of the construct by the amplifiable gene. For the neo gene or the herpes tk gene, one could employ a medium for growth of the transformants of about 0.1–1 g/ml of G418 or HAT medium respectively. Where DHFR is the amplifiable gene, the selective medium may include from about 0.01–0.25 $\mu$M of methotrexate.

In carrying out the homologous recombination, the DNA will be introduced into the primary cells. Techniques which may be used include calcium phosphate/DNA co-precipitates, microinjection of DNA into the nucleus, electroporation, bacterial protoplast fusion with intact cells, transfection, polycations, e.g., polybrene, polyornithine, etc., or the like. The DNA may be single or double stranded DNA, linear or circular. For various techniques for transforming mammalian cells, see Keown et al., *Methods in Enzymology* (1989), Keown et al., *Methods and Enzymology* (1990) Vol. 185, pp. 527–537 and Mansour et al., *Nature,* 336:348–352, (1988).

Upstream and/or downstream from the target region construct may be a gene which provides for identification of whether a double crossover has occurred. For this purpose, the herpes simplex virus thymidine kinase gene may be employed since the presence of the thymidine kinase gene may be detected by the use of nucleoside analogs, such as acyclovir or gancyclovir, for their cytotoxic effects on cells that contain a functional HSV-tk gene. The absence of sensitivity to these nucleoside analogs indicates the absence of the thymidine kinase and, therefore, where homologous recombination has occurred, that a double crossover event has also occurred.

The presence of the marker gene as evidenced by resistance to a biocide or growth in a medium which selects for the presence of the marker gene, establishes the presence and integration of the target construct into the host genome. No further selection need be made at this time, since the selection will be made in the secondary expression host, where expression of the amplified target gene may be detected. If one wishes, one can determine whether homologous recombination has occurred by employing PCR and sequencing the resulting amplified DNA sequences. If desired, amplification may be performed at this time by stressing the primary cells with the appropriate amplifying reagent, so that multi-copies of the target gene are obtained. Alternatively, amplification may await transfer to the secondary cell expression host.

High molecular weight DNA, greater than about 20 kb, preferably greater than about 50 kb DNA or preferably metaphase chromosomes are prepared from the primary recipient cell strain having the appropriate integration of the amplification vector. Preparation and isolation techniques are described by Nelson and Housman, In *Gene Transfer* (ed. R. Kucherlapati) Plenum Press, 1986. The DNA may then be introduced in the same manner as described above into the secondary host expression cells, using the same or different techniques than employed for the primary cells. Various mammalian expression hosts are available and may be employed. These hosts include CHO cells, monkey kidney cells, C127 mouse fibroblasts, 3T3 mouse cells, Vero cells, etc. Desirably the hosts will have a negative background for the amplifiable gene or a gene which is substantially less responsive to the amplifying agent.

The transformed cells are grown in selective medium containing about 0.01–0.5 $\mu$M methotrexate and, where another marker is present, e.g., the neo gene, the medium may contain from about 0.1–1 mg/ml G418. The resistant colonies are isolated and may then be analyzed for the presence of the construct in juxtaposition to the target gene. This may be as a result of detection of expression of the target gene product, where there will normally be a negative background for the target gene product, use of PCR, Southern hybridization, or the like.

The cells containing the construct are then expanded and subjected to selection and amplification with media containing progressively higher concentrations of the amplifying reagent, for example, 0.5–200 $\mu$M of methotrexate for the DHFR gene, and may be analyzed at each selection step for production of the target product. Expansion will include at least duplication and may result in at least 5 copies, preferably 10 copies or more in a tandem relationship. Thus protein production will be increased at least 1.5 fold from expression from a single copy, usually at least 3 fold, preferably at least 5 fold.

The various clones may then be screened for optimum stable production of the target product and these clones may then be expanded and used commercially for production in culture. In this manner, high yields of a product may be obtained, without the necessity of isolating the message and doing the various manipulations associated with genetic engineering or isolating the genomic gene, where very large genes can be a major research and development effort.

The following examples are offered by way of illustration and not by way of limitation.

EXPERIMENTAL

Cells

Normal human diploid skin fibroblasts, ("primary recipient") are propagated in EEMEM medium supplemented with 20% fetal calf serum. Dihydrofolate reductase (DHFR) deficient Chinese hamster ovary (CHO) DUKX-B11 cells (Urlaub and Chasin, *Proc. Natl. Acad. Sci. USA* 77:4216–4220 (1980)) ("secondary recipient") are propagated in alpha-medium supplemented with 10% dialyzed fetal bovine serum.

DNA Vector

The amplification vector is constructed from pUC19 (Yanisch-Perron et al., *Gene* 33:103–119 (1985)). A 1.8 kb HaeII fragment containing a hygromycin B phosphotransferase gene (hph) driven by the herpes simplex virus thymidine kinase (HSV tk) promoter is isolated from pHyg (Sugden et al., *Mol. Cell. Biol.* 5:410–413 (1985)) by digestion with HaeII and gel electrophoresis. Synthetic adaptors are added onto this fragment to convert the HaeII ends into HindIII ends and the resulting fragment is joined to pUC19 digested with HindIII. The resulting plasmid pUCH contains the hygromycin cassette such that transcription of hph and beta-lactamase are in the opposite orientation. A 1.3 kb SalI fragment containing a DHFR gene driven by SV40 transcriptional signals is isolated from pTND (Connors et al., *DNA* 7:651–661 (1988)) by digestion with SalI and gel electrophoresis. This fragment is ligated to pUCH digested with SalI. The resulting plasmid pUCD contains the DHFR cassette such that DHFR and are transcribed in the same direction. A 1.76 kb BamHI fragment from the phage F15 (Friezner Degen et al., *J. Biol. Chem.* 261:6972–6985 (1986)) which contains 1.45 kb of DNA flanking the transcriptional start of human tissue plasminogen activator (t-PA) in addition to the first exon and part of the first intron is isolated by gel electrophoresis after BamHI digestion. This fragment is joined to pUCD following digestion of the latter with BamHI. The resulting plasmid pUCG has the promoter of the t-PA fragment oriented opposite to that of the DHFR cassette. The t-PA fragment contains a single NcoI site, which is not unique to pUCG. A partial NcoI digest is carried out and a NotI linker is inserted. The resulting plasmid pCG contains a unique NotI site in the t-PA fragment which allows the plasmid to be linearized prior to transformation of the primary human diploid fibroblasts in order to increase the frequency of homologous recombination (Kucherlapati et al., *Proc. Natl. Acad. Sci. USA* 81:3153–3157 (1984)).

Preparation of Primary Recipients

The plasmid pCG linearized with NotI is introduced into the primary recipients by electroporation employing DNA at 10 nM. The resulting cells are then grown in selective medium (EEMEM with 200 μg/ml hygromycin B). Resistant colonies are isolated and analyzed by PCR (Kim and Smithies, *Nucleic Acids Res.* 16:8887–8903 (1988)) using as primers the sequences (SEQ ID NO:2) GCGGCCTCGGC-CTCTGCATA and (SEQ ID NO:3) CATCTCCCCTCTG-GAGTGGA to distinguish homologous integrants from random ones. Amplification of cellular DNA by PCR using these two primers yields a fragment of 1.9 kb only when DNA from correctly targeted cells is present. Cells comprising the DHFR gene integrated into the t-PA region are expanded and used as a source of genetic material for preparation of secondary recipients.

Preparation of Secondary Recipients

Metaphase chromosomes are prepared Nelson et al., *J. Mol. Appl. Genet.* 2:563–577 (1984)) from recipients demonstrating homologous recombination with the DHFR and are then transformed in DHFR-deficient CHO cells by calcium phosphate mediated gene transfer (Nelson et al., *J. Mol. Appl. Genet.* 2:563–577 (1984)). The cells are then grown in selective medium (alpha-medium containing 200 μg/ml hygromycin B). Resistant colonies are isolated and analyzed for expression of human t-PA (Kaufman et al., *Mol. Cell. Biol.* 5:1750–1759 (1985)). The cell clones are then grown in selective medium containing progressively higher concentrations of methotrexate (0.02–80 μM, with steps of 4-fold increases in concentration). After this amplification procedure, the cells are harvested and the human t-PA is analyzed employing an ELISA assay with a monoclonal antibody specific for t-PA (Weidle and Buckel, *Gene* 51:31–41 (1987)). Clones providing for high levels of expression of t-PA are stored for subsequent use.

Isolation of a Genomic Clone Containing Sequences for Targeting Erythropoietin A clone was obtained by screening a human placental DNA genomic library (Clontech) in EMBL 3-SP6/T7 using two 36 bp oligonucleotide probes (SEQ ID NO:4) 5'-CTGGGTTGCTGAGTTCCGCAAAGTAGCTGGGTC-TGG-3' and (SEQ ID NO:5) 5'-CGGGGGTCGGGGCT-GTTATCTGCATGTGTGCGTGCG-3' to the presumed promoter region of human erythropoietin. From this clone two subclones were created in pSP72 (Krieg and Melton (1987) Meth. Enzymol. 155, 397–415), one containing a 5 kb BamHI-HindIII fragment from the region upstream to the coding region of EPO (pTD.1) and one containing a 5 kb HindIII-BamHI fragment coding for EPO (pTD.2).

Construction of DNA Fragment for Targeting Erythropoietin

Figures 1, 2:
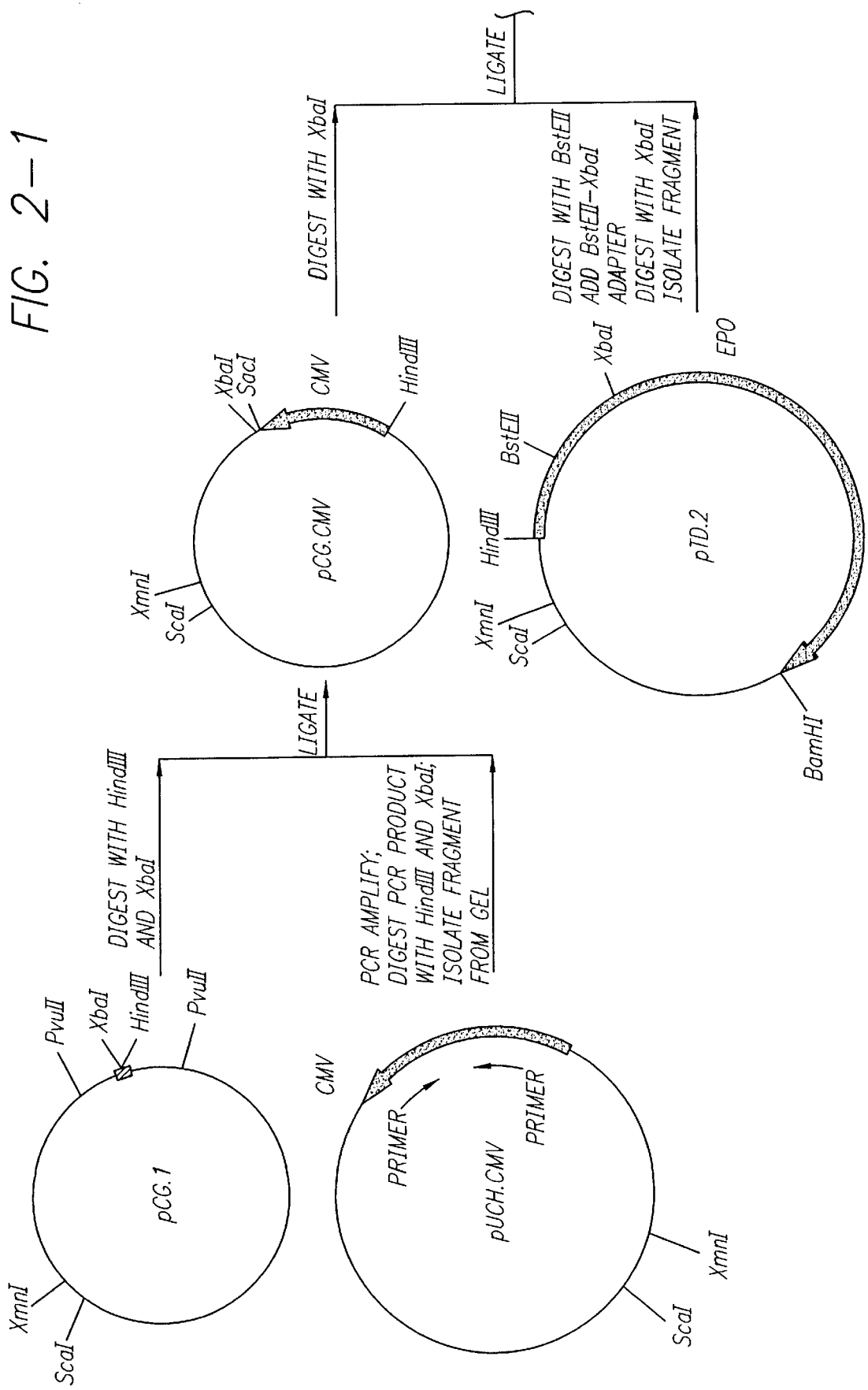
FIG. 2 is a diagrammatic illustration of the construction of the plasmid pCG.HR1.
Figure 2:
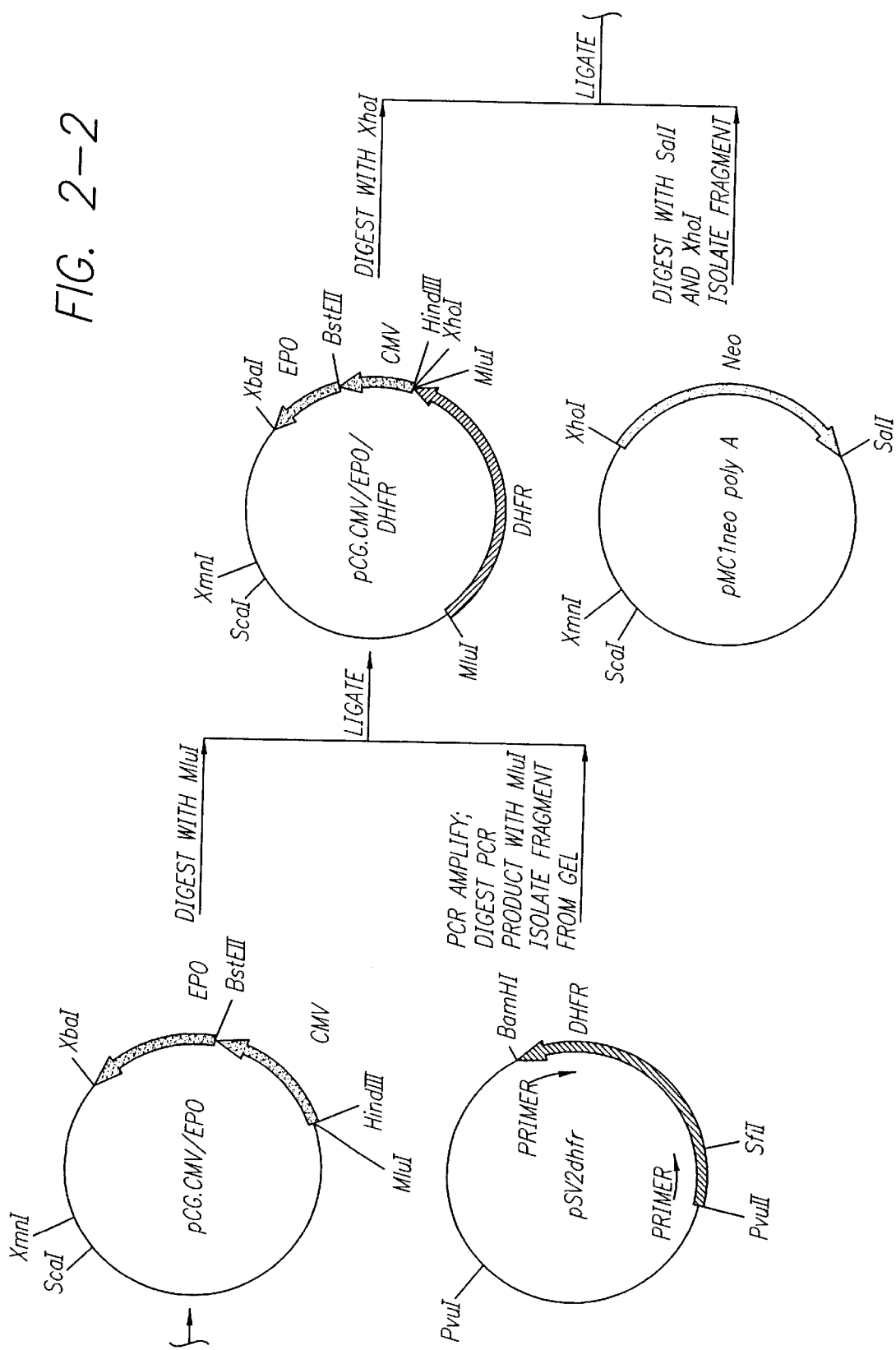

A plasmid pCG.1 was constructed by replacement of the polylinker of pBluescript SK(−) (Stratagene) between the SacI and XpnI sites with a synthetic double stranded 72 base pair DNA fragment (FIG. 1). Referring to FIG. 2, into pCG.1 was cloned between the HindIII and XbaI sites a 678 bp fragment containing the enhancer and promoter of the immediate early gene of human cytomegalovirus (CMV, Boshart et al (1985) Cell 41, 521–530) obtained by a PCR amplification of the plasmid pUCH.CMV (gift of M. Calos, Stanford U.) using the oligonucleotide primers (SEQ ID NO:6) 5'-CGCCAAGCTTGGCCATTGCATACGTT-3' and (SEQ ID NO:7) 5'-GAGGTCTAGACGGTTCACTAAA-CGAGCTCT-3' in order to engineer HindIII and XbaI sites respectively onto the ends of the resultant fragment. The resultant plasmid pCG.CMV was used for further constructions.

The 620 bp BstEII-XbaI fragment from the pTD.2 was joined by the use of a BstEII-XbaI adapter to pCG.CMV restricted with XbaI to create the plasmid pCG.CMV/EPO, in which the BstEII site of the EPO fragment is next to the promoter end of the CMV fragment. Into pCG.CMV/EPO was cloned successively a 1.94 kb fragment encoding methotrexate resistance from the plasmid pSV2dhfr (Subramani et al (1981) Mol. Cell. Biol. 1, 854–864) and a 1.15 kb fragment encoding G418 resistance from the plasmid pMClneo polyA (Thomas and Capecchi (1987) Cell 51, 503–512). The neo gene was obtained as an XhoI-SalI fragment and the dhfr gene was obtained by PCR amplification using the primers (SEQ ID NO:8) 5'-GGACGCGTGGATCCAGACATGATAAGATA-3' and (SEQ ID NO:9) 5'-GGACGCGTCAGCTGTGGAAT-GTGTGTCAG-3' designed to add MluI sites at the ends of the resultant fragment. The neo and dhfr genes were cloned into the XhoI and MluI sites respectively of pCG.CMV/EPO to give the plasmids pCG.CMV/EPO/DHFR and pCG.CMV/EPO/Neo/DHFR such that their transcription is in the same orientation as that of CMV. Finally, the 5 kb BamHI-HindIII fragment from pTD.1 was added via ClaI adapters at the ClaI site of pCG.CMV/EPO/Neo/DHFR to give pCG.HR1. In pCG.HR1, the 5' 5 kb EPO fragment is in the same orientation as that of the 620 bp BstEII-XbaI fragment with respect to the original lambda clone.

Figures 2, 3:
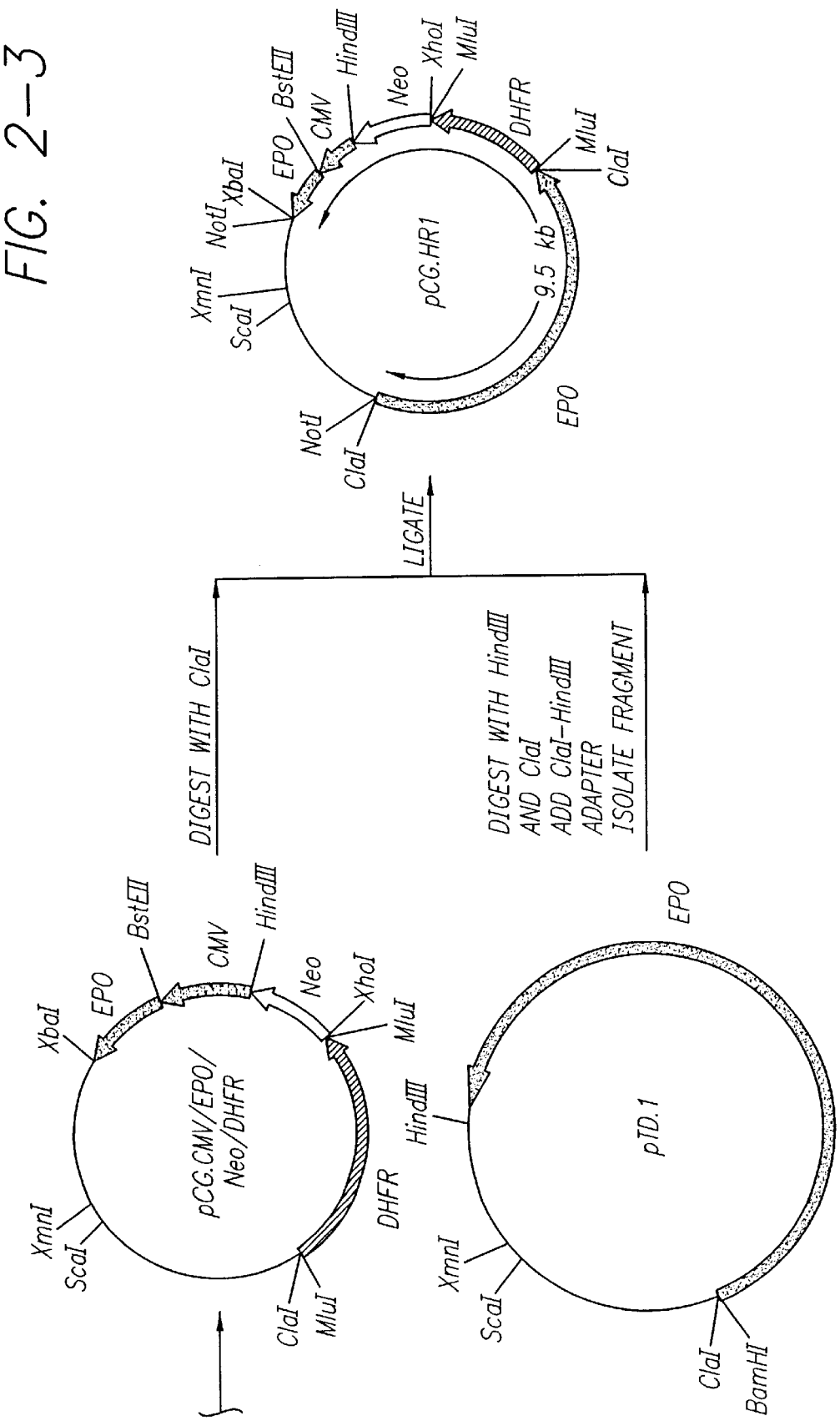
FIG. 3 is a diagrammatic illustration of the result of targeting the EPO locus by homologous recombination with the DNA from pCG.HR1 cut with NotI.
Figure 3:
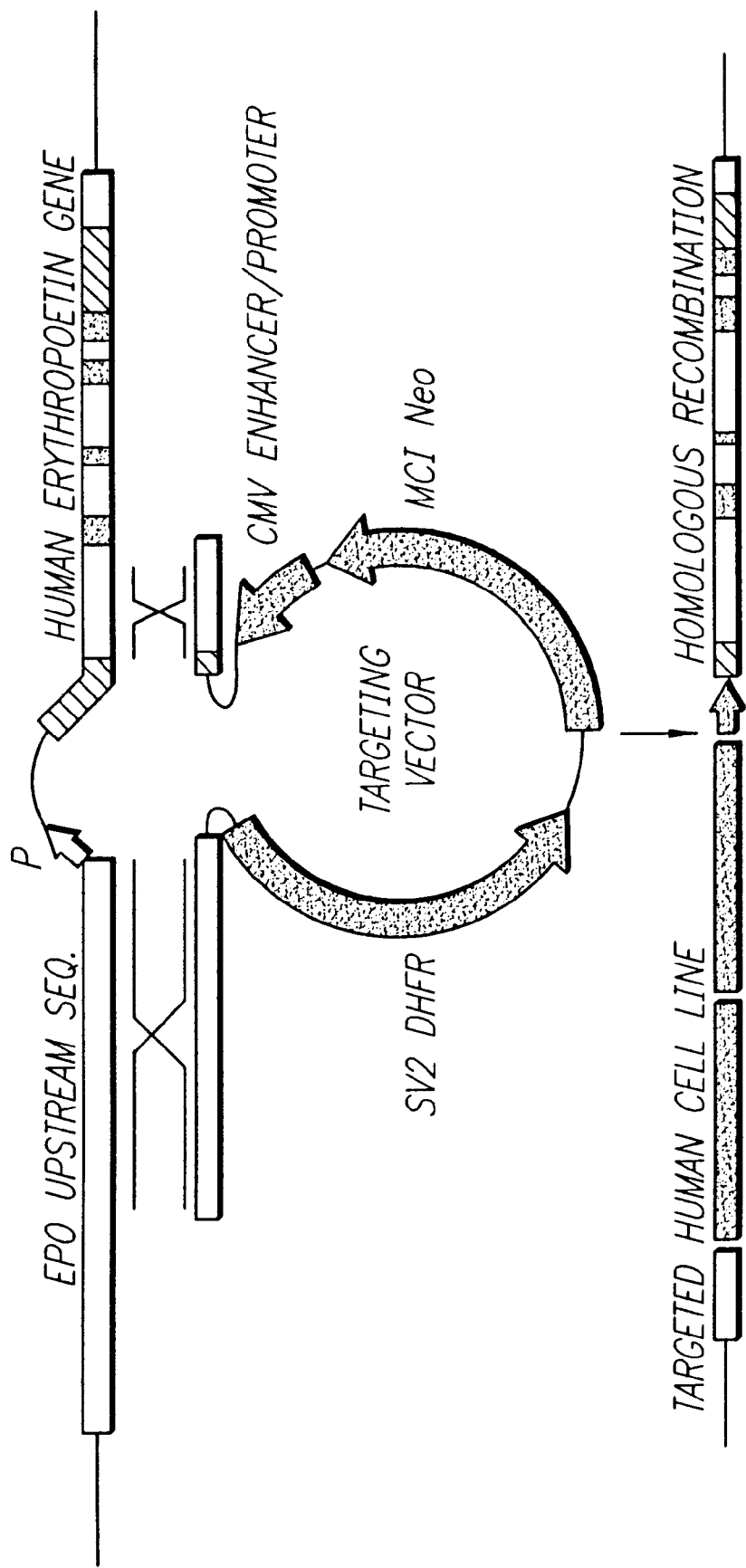

A 9.54 kb fragment containing the 5' 5 kb BamHI-HindIII EPO fragment, the dhfr and G418 markers, the CMV enhancer/promoter and the 620 bp BstEII-XbaI EPO fragment can be released from pCG.HR1 as a NotI or SacII fragment. This NotI fragment can be used for homologous recombination as it is designed to serve as an omega structure in recombination having 5 kb and 620 bp of homology to facilitate the event (FIG. 3).

For electroporation, the DNA was first cut with NotI, then extracted with phenol/chloroform and precipitated by the addition of ethanol before centrifugation. The resultant DNA pellet was resuspended at a concentration of 2 mg/ml in a volume (10 μl) of 10 mM Tris-HCl, 1 mM EDTA (TE).

Introduction of DNA Into Cells

Transformed primary human 293 embryonal kidney cells (ATCC CRL 1573) were cultured in Cellgro DMEM H16 (Mediatech) supplemented with 10% calf serum, glutamine (2 mM) and penicillin (100 U/ml)/streptomycin (0.1 mg/ml) and grown at 37° C. in 5% $CO_2$. At 90% confluency, cells were prepared for electroporation by trypsinization, concentration by brief centrifugation and resuspension in PBS at $10^7$ cells/0.8 ml. The cells were equilibrated at 4° C., and DNA (50 μg) restricted with NotI (as described above) was added. The mixture was electroporated at 960 μF and 260 V with a BioRad Gene Pulser and then iced again for 10 min before plating onto a 10 cm dish. After incubation at 37° C. for 48 hr, the cells from a 10 cm dish were split equally among 5 24-well plates in media containig G418 at 0.6 mg/ml (effective concentration). Under these electroporation conditions, 4–10 colonies/well survive drug selection after 2 weeks.

Detection of Homologous Recombination by PCR Analysis

Figure 4:
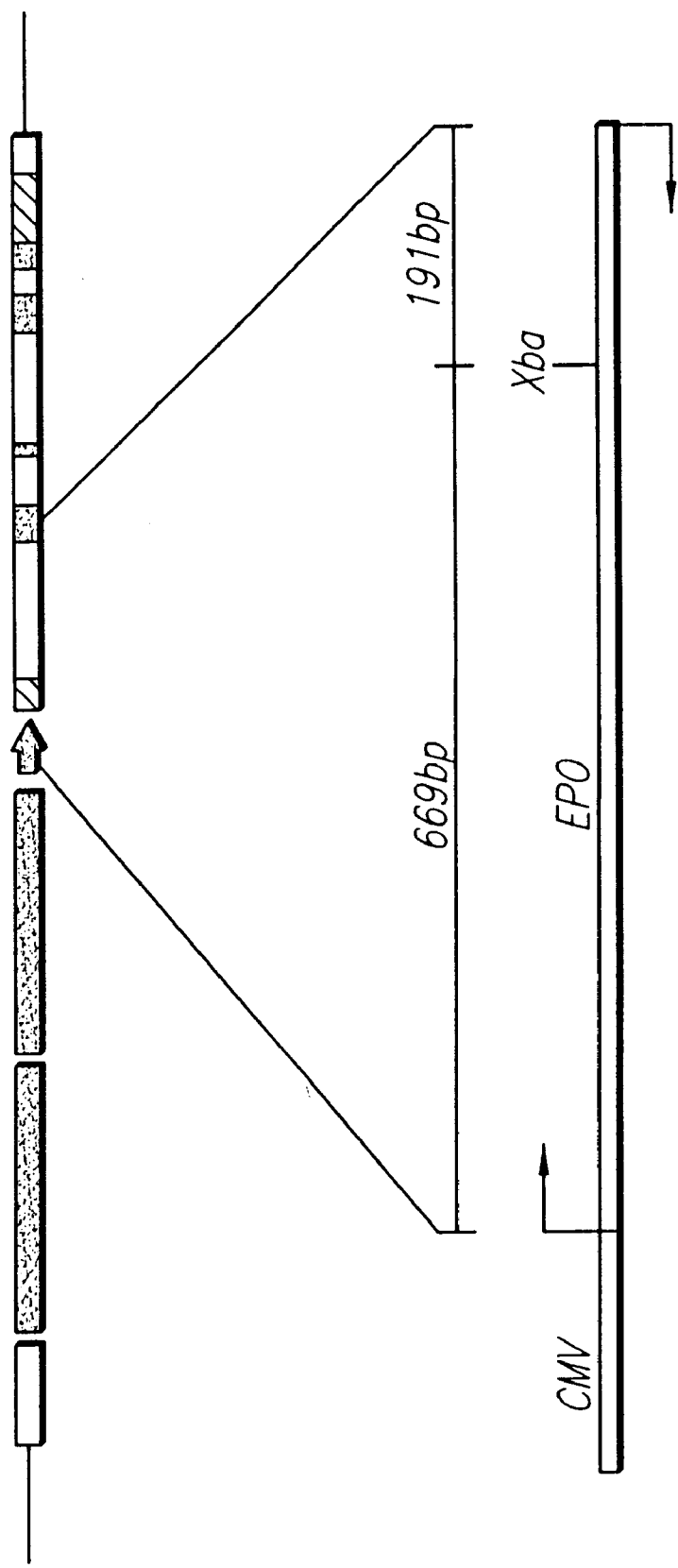
FIG. 4 is a diagrammatic illustration of the PCR amplification fragment produced from cells in which a homologous recombination event has occurred.

Using NotI restricted DNA from pCG.HR1, successful homologous recombination is obtained by insertion of the 3.8 kb construct at the targeted EPO locus while simultaneously deleting 1.2 kb of genomic sequence (FIG. 3). PCR is used to detect unique targeting events versus random integration of the DNA as diagrammed in FIG. 4. Two primers are synthesized, one to the 3' end of CMV and the other to the region 3' to the XbaI site used for the 620 bp BstEII-XbaI fragment in the targeting DNA. A homologous recombination event generates a DNA target in the genome from which these primers produce an amplification product of 860 bp.

In order to detect the targeting event, pools of clones (from the electroporated 293 cells) from 4 wells each (representing about 16 colonies) were generated by trypsinizing wells and using 90% of each well for the pool. The remaining 10% of each well was then reseeded back into the well. Genomic DNA was then prepared from each pool as follows. The cells in each pool were pelleted by centrifugation for 2 min. in a 1.5 ml microcentrifuge tube, resuspended in PBS (20 μl), and treated for 1 hr at 37° C. with a solution (400 μl) containing 10 mM Tris-HCl (pH7.5), 100 mM NaCl, 5 mM EDTA, 1% SDS and RNase A (40 μg/ml). Proteinase K (10 μl, 10 mg/ml) was then added, and the samples were incubated for 4 hr at 50° C. before extractions by vigorous vortexing with phenol/chloroform (200 μl each), then with chloroform (400 μl), the addition of ethanol (800 μl), and centrifugation at 25° C. for 10 min. The DNA pellets were washed with 70% ethanol, dried and resuspended in TE (20 μl). An average of 40 μg of genomic DNA was obtained from each sample.

Approximately 1 μg from each sample of genomic DNA was used for PCR analysis. The DNA in a volume (10 μl) of TE was boiled for 10 min. prior to the addition of PCR mix (40 μl). The reaction (50 μl) contained 10 mM Tris-HCl (pH 9.0 at 25° C.), 50 mM KCl, 1.5 mM $MgCl_2$, 0.01% gelatin, 0.1% Triton X-100, 200 μM dNTPs, 1 μM each of the primers (SEQ ID NO:10) 5'-AAGCAGAGCTCGTTT-AGTGAACCG-3' and (SEQ ID NO:11) 5'-TGAGCGTGAGTTCTGTGGAATGTG-3', and 1.5 U of Taq DNA polymerase (Promega). Following an initial incubation of 94° C. for 3 min, the samples were subjected to 45 cycles of denaturation at 94° C. for 1 min., annealing at 66° C. for 1.5 min. and extension at 72° C. for 2 min. At the end of the 45 cycles, the samples were incubated an additional 5 min. at 72° C. A portion (20 μl) of each sample was analyzed on a 1% agarose gel run in TBE and stained with ethidium bromide. Out of the 90 pools analyzed from 3 electroporations, two samples were identified which exhibited the correct size fragment by ethidium bromide staining. The DNA from the PCR reaction was recovered and subjected to restriction mapping with XbaI. The correct amplification product should upon treatment with XbaI yield two fragments, 669 bp and 191 bp. The samples from the two pools both yield fragments of the correct sizes. In addition, the sample from pool 1 exhibits other bands in the uncut material.

Following the procedure described previously, metaphase chromosomes are prepared from the recipients demonstrating homologous recombination with DHFR and transformed in DHFR deficient CHO cells. After isolating resistant colonies and analyzing for expression of EPO, the cell clones are grown in selective medium containing progressively higher concentrations of methotrexate (0.02–80 μM) with steps of 4-fold increases in concentration. The cells are then harvested, cloned and screened for production of EPO. Clones providing for at least 2-fold enhancement of EPO production are isolated.

It is evident from the above results, that the subject method provides for a novel approach to expression of a wide variety of mammalian genes of interest. The method is simple, only requires the knowledge of a sequence of about 300 bp or more in the region of a target gene, and one may then use substantially conventional techniques for transferring the amplifiable region to an expression host, and production of the desired product in high yield.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for large scale production of a mammalian target gene product in cell culture, comprising:
   (1) culturing a mammalian continuous cell line which was prepared by the steps of:
      (a) integrating, via targeted homologous recombination, a nucleotide regulatory sequence heterologous to the target gene, into the genome of a mammalian host cell, so that the integrated nucleotide regulatory sequence is operably associated with the mammalian target gene contained in the host cell genome to form a recombined mammalian target gene; and
      (b) transferring the recombined mammalian target gene to a mammalian continuous cell line compatible with the integrated nucleotide regulatory sequence, so that the mammalian target gene product is expressed by the mammalian continuous cell line in culture; and
   (2) recovering the mammalian target gene product from the cell culture.

2. The method of claim 1 in which the mammalian continuous cell line further contains an amplifiable gene operatively associated with the mammalian target gene controlled by the heterologous nucleotide regulatory sequence, and the mammalian continuous cell line is cultured under conditions that amplify the amplifiable gene and the mammalian target gene, so that expression of the mammalian target gene controlled by the heterologous nucleotide regulatory sequence is enhanced, in which the mammalian continuous cell line was prepared by:
   (a) integrating, via targeted homologous recombination, the amplifiable gene within an intron or proximal to the mammalian target gene contained in the mammalian host cell, so that the amplifiable gene and the heterologous regulatory sequence are operatively associated with the mammalian target gene; and
   (b) transferring the recombined mammalian target gene to a mammalian continuous cell line, so that the expressed mammalian target gene controlled by the heterologous regulatory sequence is amplified when the mammalian continuous cell line is cultured under conditions that amplify the amplifiable gene.

3. A method for producing a mammalian continuous cell line used for large-scale protein production in culture, comprising:
   (a) integrating, via targeted homologous recombination, a nucleotide regulatory sequence heterologous to a mammalian target gene contained in a mammalian host cell, so that the integrated nucleotide regulatory sequence is operably associated with the mammalian target gene to form a recombined mammalian target gene; and
   (b) transferring the recombined mammalian target gene to a mammalian continuous cell line compatible with the integrated nucleotide regulatory sequence, so that the mammalian target gene product is expressed by the mammalian continuous cell line in culture.

4. The method for producing the mammalian continuous cell line of claim 3, which further comprises:
   (a) integrating, via targeted homologous recombination, an amplifiable gene within an intron or proximal to the mammalian target gene contained in the mammalian host cell, so that the amplifiable gene and the heterologous regulatory sequence are operably associated with the mammalian target gene; and
   (b) transferring the recombined mammalian target gene to a mammalian continuous cell line, so that the expressed mammalian target gene controlled by the heterologous regulatory sequence is amplified when the mammalian continuous cell line is cultured under conditions that amplify the amplifiable gene.

5. The method of claim 2 or 4 in which the amplifiable gene is dihydrofolate reductase, metallothionein-I, metallothionein-II, adenosine deaminase, ornithine decarboxylase, or glutamine synthetase.

6. The method of claim 1, 2, 3 or 4 in which the mammalian host cell is a human cell.

7. The method of claim 1, 2, 3 or 4 in which the mammalian host cell is a primary cell.

8. The method of claim 7 in which the primary mammalian cell is a fibroblast, lymphocyte, epithelial or endothelial cell.

9. The method of claim 1, 2, 3 or 4 in which the mammalian target gene is a human gene.

10. The method of claim 9 in which the target gene encodes an interleukin, a growth factor, a colony stimulating factor, erythropoietin, a plasminogen activator, an enzyme, an interferon, or a receptor protein.

11. The method of claim 1, 2, 3 or 4 in which the heterologous regulatory sequence is a viral promoter or a promoter/enhancer.

12. The method of claim 11 in which the promoter/enhancer is a cytomegalovirus promoter/enhancer.

13. The method of claim 1, 2, 3 or 4 in which the mammalian continuous cell line is a Chinese hamster ovary cell line, a monkey kidney cell line, a C127 mouse fibroblast cell line, a 3T3 mouse cell line, a Vero call line or a 293 cell line.

14. A mammalian continuous cell line, the genome of which contains a heterologous genomic DNA encoding a gene product of interest operatively associated with (a) a nucleotide regulatory sequence different from the wild-type regulatory sequence normally associated with the heterologous genomic DNA, and (b) an amplifiable gene, so that expression of the heterologous genomic DNA is controlled by the regulatory sequence and is amplified when the mammalian continuous cell line is cultured under conditions that amplify the amplifiable gene.

15. The mammalian continuous cell line of claim 14 in which the heterologous genomic DNA is a human gene.

16. The mammalian continuous cell line of claim 15 in which the human gene encodes an interleukin, a growth factor, a colony stimulating factor, erythropoietin, a plasminogen activator, an enzyme, an interferon or a receptor protein.

17. The mammalian continuous cell line of claim 14 in which the regulatory sequence is a viral promoter or promoter/enhancer.

18. The mammalian continuous cell line of claim 17 in which the promoter/enhancer is a cytomegalovirus promoter/enhancer.

19. The mammalian continuous cell line of claim 14 in which the amplifiable gene is dihydrofolate reductase, metallothionain-I, Metallothionein-II, adenosine deaminase, ornithine decarboxylase, or glutamine synthetase.

20. The mammalian continuous cell line of claim 14 which is a Chinese hamster ovary cell line, a monkey kidney cell line, a C127 mouse fibroblast cell line, a 3T3 mouse cell line, a VERO cell line or a 293 cell line.

* * * * *